United States Patent [19]

Atkinson et al.

[11] Patent Number: 5,565,330
[45] Date of Patent: Oct. 15, 1996

[54] **METHOD FOR REMOVING N-TERMINAL DIPEPTIDES FROM PRECURSOR POLYPEPTIDES WITH DIPEPTIDYLAMINOPEPTIDASE FROM *DICTYOSTELIUM DISCOIDEUM***

[75] Inventors: Paul R. Atkinson; Matthew D. Hilton; Peter K. Lambooy, all of Indianapolis, Ind.

[73] Assignee: Eli Lilly and Company, Indianapolis, Ind.

[21] Appl. No.: 445,308

[22] Filed: May 19, 1995

Related U.S. Application Data

[62] Division of Ser. No. 301,519, Sep. 7, 1994, which is a continuation of Ser. No. 955,539, Oct. 1, 1992, abandoned.

[51] Int. Cl.⁶ ............... C12P 21/06; C12N 9/48; C12N 9/58
[52] U.S. Cl. ............ 435/68.1; 435/212; 435/223
[58] Field of Search .................. 435/68.1, 212, 435/223

[56] References Cited

U.S. PATENT DOCUMENTS

| | | | |
|---|---|---|---|
| 4,743,549 | 5/1988 | Mayr et al. | 435/191 |
| 4,894,439 | 1/1990 | Donn et al. | 530/351 |
| 4,929,700 | 5/1990 | Halenbeck et al. | 530/351 |
| 5,075,222 | 12/1991 | Hannum et al. | 435/69.1 |
| 5,126,249 | 6/1992 | Becker et al. | 435/68.1 |
| 5,157,112 | 10/1992 | Van Snick et al. | 530/387.9 |
| 5,173,409 | 12/1992 | English | 435/71.1 |
| 5,175,251 | 12/1992 | Johnson et al. | 530/324 |
| 5,177,003 | 1/1993 | Shay et al. | 435/71.1 |
| 5,179,196 | 1/1993 | Johnson et al. | 530/350 |
| 5,188,969 | 2/1993 | Arai et al. | 435/548 |

FOREIGN PATENT DOCUMENTS

| | | |
|---|---|---|
| 0397420 | 4/1990 | European Pat. Off. . |
| 0217814 | 5/1990 | European Pat. Off. . |

OTHER PUBLICATIONS

Chan, et. al., 1985, *Biochem. Biophys. Res. Comm.*, 127(3): 962–968.
Chan, et. al., 1987, *Experimental Mycology*, 11: 27–35.
Huang, et. al., 1992, *Experimental Mycology*, 16: 102–109.

*Primary Examiner*—John W. Rollins
*Assistant Examiner*—Jon P. Weber
*Attorney, Agent, or Firm*—Ronald S. Maciak; Douglas K. Norman

[57] ABSTRACT

A method for removing dipeptides from the amino terminus of precursor polypeptides to produce a polypeptide product is presented which comprises contacting the precursor polypeptide for sufficient time to remove the dipeptide with a dipeptidylaminopeptidase (dDAP) from the slime mold, *Dictyostelium descoideum*, which has a mass of about 225 kilodaltons and a pH optimum of about 3.5. The precursor polypeptides may be made recombinantly and may be analogs of naturally occurring polypeptides.

22 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Met Asp Phe Pro Ala Met Ser Leu
1               5

( 2 ) INFORMATION FOR SEQ ID NO:2:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Phe Pro Ala Met Ser Leu
1               5

( 2 ) INFORMATION FOR SEQ ID NO:3:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Met Arg Met Tyr Phe Val Asn Gln His Leu
1               5                   10

( 2 ) INFORMATION FOR SEQ ID NO:4:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

Met Tyr Phe Val Asn Gln His Leu
1               5

( 2 ) INFORMATION FOR SEQ ID NO:5:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Phe Val Asn Gln His Leu
1               5

METHOD FOR REMOVING N-TERMINAL DIPEPTIDES FROM PRECURSOR POLYPEPTIDES WITH DIPEPTIDYLAMINOPEPTIDASE FROM *DICTYOSTELIUM DISCOIDEUM*

This application is a division, of application Ser. No. 08/301,519, filed Sep. 7, 1994, now allowed, which is a continuation of application Ser. No. 07/955,539, filed Oct. 1, 1992, now abandoned.

FIELD OF THE INVENTION

This invention is in the field of biotechnology. More specifically, this invention concerns a dipeptidylaminopeptidase isolated from the slime mold, *Dictyostelium discoideum*, which is useful in the processing of recombinantly produced biological compounds.

BACKGROUND OF THE INVENTION

*Dictyostelium descoideum* is a primitive eukaryotic microorganism commonly called a slime mold, or more specifically, a cellular slime mold. The name is derived from the two extreme states of the microorganism from a macroscopic perspective. When actively growing, the *D. discoideum* grow as single cell amoeba. At this stage they have no cell wall, hence their appearance as a thin film (or slime). Upon starvation on a solid medium, the independent cells aggregate to form a colony. The colony exhibits traits of a multicellular organism in that it migrates in the form called a slug and then differentiates, with the posterior cells of the slug forming a foot, the anterior cells forming a stalk and the middle cells forming a fruiting body. The organism is found naturally on the surface of soil and dung. The wild type amoeba obtains nutrients exclusively by ingestion (phagocytosis) of whole bacteria; for this reason they are sometimes referred to as carnivorous. Axenic mutants of *D. discoideum* have been isolated which are capable of growth without coculture of "food" bacteria and which therefore can be grown on soluble media. The present invention relates to a novel dipeptidylaminopeptidase isolated from *D. discoideum*.

Dipeptidylaminopeptidases (DAP) are enzymes which hydrolyze the penultimate amino terminal peptide bond releasing dipeptides from the unblocked amino-termini of peptides and proteins. There are currently four classes of dipeptidylaminopeptidases (designated DAP-I, DAP-II, DAP-III and DAP-IV) which are distinguished based on their physical characteristics and the rates at which they catalyze cleavage with various amino-terminal peptide sequences. DAP I is a relatively non-specific DAP that will catalyze the release of many dipeptide combinations from the unblocked amino termini of peptides and proteins. DAP I shows little or no activity if the emergent dipeptide is X-Pro, Arg-X, or Lys-X (where X is any amino acid). DAP II shows a preference for amino terminal dipeptide sequences that begin with Arg-X or Lys-X, and to a lesser extent, X-Pro. DAP-II exhibits significantly lower cleavage rates versus most other dipeptide combinations. DAP III appears to have a propensity toward amino terminal dipeptide sequences of the form Arg-Arg and Lys-Lys. DAP IV shows its highest rate of hydrolytic activity toward dipeptide sequences of the form X-Pro. The DAP enzymes, particularly DAP-I and DAP-IV, have been shown to be useful in processing proteins. The present invention concerns a novel DAP from *Dictyostelium descoideum* which is useful in processing recombinant proteins with an even numbered amino acid N-terminal extension.

SUMMARY OF THE INVENTION

The present invention is directed to a novel dipeptidylaminopeptidase isolated from the cellular slime mold, *Dictyostelium descoideum*. The novel DAP enzyme, dDAP, displays an activity which is somewhat similar to both DAP-I and DAP-III but is highly distinctive from these enzymes in physical and other enzymatic characteristics. The invention is also directed to methods for using the dDAP enzyme to remove dipeptides from the N-terminus of recombinantly produced precursor proteins or peptides. The dDAP enzyme of the present invention can be used to remove single dipeptides from the N-terminus of polypeptides and can also be used to sequentially remove more than one dipeptide from the N-terminus of precursor polypeptides. In addition, the invention relates to methods for isolating and purifying the dDAP enzyme from cultures of *D. discoideum*.

For purposes of the present invention, as disclosed and claimed herein, the following terms and abbreviations are as defined below.

dDAP—a dipeptidylaminopeptidase, isolated from *Dictyostelium descoideum*, which demonstrates a pH optimum of about pH 3.5 with GFpNA as a substrate and has a native molecular weight of about 225,000 daltons, as measured by analytical ultracentrifugation, and a subunit molecular weight of about 66,000 daltons, as measured by SDS polyacrylamide gel electrophoresis.

GFpNA—Gly-Phe p-nitroanilide

Precursor polypeptide—a recombinantly produced polypeptide which comprises an even number of amino acids extended from the amino terminus of the desired polypeptide of interest.

Processed polypeptide—a polypeptide wherein the N-terminal dipeptide or dipeptides have been removed to yield the desired polypeptide of interest.

RRBNA—Arg-Arg-β-naphthylamide

All amino acid abbreviations used in this disclosure are those accepted by the United States Patent and Trademark Office as set forth in 37 C.F.R. §1.822(b)(2) (1990).

DETAILED DESCRIPTION OF THE INVENTION

The present invention is directed to dDAP, a dipeptidylaminopeptidase isolated from the cellular slime mold *Dictyostelium descoideum*. The dDAP enzyme displays a propensity to cleave unblocked amino terminal sequences traditionally associated with both DAP-I and DAP-III, yet dDAP is highly distinctive from these enzymes both in physical and other enzymatic characteristics. dDAP demonstrates a pH optimum of about pH 3.5 with GFpNA as a substrate and has a native molecular weight of about 225,000 daltons and a subunit molecular weight of about 66,000 daltons. Lectin affinity chromatography demonstrates that the dDAP enzyme is likely a glycoprotein. The dDAP enzyme has the ability to remove dipeptides from the synthetic substrates, Gly-Phe paranitroanilide (GFpNA) and Arg-Arg-β-naphthylamide (RRBNA), as well as from numerous other synthetic and recombinantly-produced polypeptides.

Known DAP-I enzymes have been isolated from a wide variety of animals and animal tissue. The new enzyme, dDAP, is isolated from the culture broth of *Dictyostelium discoideum*. DAP-I enzymes require halide and reducing agents for activity. Reagents such as iodoacetate, which modify cysteine sulfhydryls, inactivate DAP-I enzymes. DAP-I has optimal activity between pH 5 and 6. By contrast, the dDAP enzyme has a pH optimum of about 3.5 with Gly-Phe-pNA or Gly-Arg-pNA as substrates, and exhibits significant activity against peptides and proteins at pH 3.5. The dDAP enzyme is devoid of significant activity above pH 6. The dDAP enzyme requires no added reducing agents and is fully active in the presence of cysteine modifiers such as iodoacetate or tetrathionate. dDAP is similar to bovine DAP-I in that it is unable to cleave peptides with blocked N-termini, yet dDAP is unlike bovine DAP-I in being active against substrates having an oxidized methionine at the N-terminus. Bovine DAP-I is unable to cleave substrates with oxidized methionines at the N-terminus. In addition, unlike bovine DAP-I, the dDAP enzyme is able to readily cleave the Arg-Arg-β-naphthylamide substrate. This ability to cleave an amino terminal Arg-Arg dipeptidyl-containing substrate is more similar to the activity of the mammalian and microbial sourced DAP-III enzymes, although the DAP-III enzyme is reported to have a pH optimum in the alkaline range, while dDAP functions most efficiently in acidic ranges. The subunit molecular weight of dDAP, as estimated by SDS PAGE, is approximately 66,000 daltons while the subunit molecular weight of mammalian DAP-I is about 22,000 daltons.

The dDAP enzyme of the present invention is most useful for converting precursor polypeptides into processed polypeptides. For instance, if human growth hormone is the desired polypeptide, one merely expresses a precursor of human growth hormone (in one case, a Met-Asp-human growth hormone), then subjects this precursor to dDAP activity to release the dipeptide Met-Asp and the desired processed polypeptide, human growth hormone. The processed peptide is not required to be the "natural" wild-type polypeptide, as often it is desirable to produce analogs or intermediates. The method of processing precursor polypeptides is also a part of the present invention. Other precursor polypeptides which may be processed by dDAP include Met-Arg-hGH, Met-Tyr-Proinsulin, Met-Arg-Proinsulin, Met-Arg-Proinsulin Analog (B28 Lys, B29 Pro), Met-Tyr-Proinsulin Analog (B28 Lys, B29 Pro), Met-Arg-Proinsulin Analog (B10 Asp, des B28–30) and Met-Tyr-Proinsulin Analog (B10 Asp, des B28–30). Insulin Analog (B28 Lys, B29 Pro) is disclosed in European Patent Application Serial No. 90301224.3 while Insulin Analog (B10 Asp, des B28–30) is disclosed in European Patent Application Serial No. 92305678.2. In addition, dDAP may be used to sequentially remove more than one set of dipeptides from the N-terminus of precursor polypeptides. Processing of Met-Arg-Proinsulin and Met-Arg-Proinsulin Analogs with bovine DAP-I is disclosed in Becker et. al., U.S. patent application No. 5,126,249, issued Jun. 30, 1992, the entire teaching of which is herein incorporated by reference.

The use of the dDAP enzyme to remove dipeptides from precursor proteins is advantageous in that dDAP has a pH optimum of about 3.5 which allows the reaction to be run at acidic pH ranges where many precursor polypeptides will be soluble. Furthermore, conversions of some precursor polypeptides at neutral pH or higher may lead to higher levels of interchain disulfide dimers or polymers of the substrate, with a concomitant loss in product yield. This phenomenon, known as disulfide scrambling, is particularly troubling when one uses bovine DAP-I, as DAP-I requires the addition of reducing agents, such as β-mercaptoethanol or cysteine, to the reaction mixture. Also, oxidation of methionine residues occurs at a lower rate in acidic pH ranges. In addition, it is more economically feasible to use an enzyme from a fermentation culture of *D. discoideum*, rather than to rely upon the commercial production of enzymes from animal sources, as fermentation technology allows for greater product consistency and enzyme reproducibility. The avoidance of animal-derived enzymes allows for a constant source of highly-purified bulk material. Fermentation of *D. discoideum* Ax3 (ATCC 28368) followed by centrifugation, anion exchange chromatography, hydrophobic interaction chromatography and size exclusion chromatography yields a highly purified solution of dDAP enzyme which can be stored or used immediately to process precursor polypeptides. The isolation and purification of dDAP from the fermentation broth is also a part of the present invention.

Conversion of precursor polypeptides into processed polypeptides can be accomplished at a wide variety of temperatures, pH ranges and time periods. The reaction is generally conducted in an aqueous medium suitably buffered to obtain and maintain a pH from about 2.5 to about 5.5. Preferably the pH of the medium ranges from about 3.0 to about 4.5, and, most preferably, from about 3.0 to about 3.5. The pH optimum may vary slightly according to the substrate. For example, the rate of processing of Gly-Phe-pNA and Gly-Arg-pNA occurs most rapidly at about pH 3.5, while the rate of processing of Met-Asp-hGH occurs readily at about pH 3.0 to about pH 3.5. The rate of processing of Arg-Arg-βNA occurs most rapidly at about pH 4.5. The skilled artisan will recognize that the pH optimum of any specific reaction will be determined by such factors as stability and solubility of the given precursor polypeptide and enzyme. In some cases, a solubilizing agent such as urea, sodium dodecylsulfate, guanidine, and the like, may be employed.

The processing reaction can be allowed to run for any given time period, ranging from only a few seconds to several days. Preferably the reaction is allowed to run from between about 1 minute to about 24 hours, and most preferably, from about 1 hour to about 8 hours. The skilled artisan will recognize that the time of the reaction can easily be adjusted to cover any parameter needed for any desired precursor polypeptide or processed polypeptide.

The temperature of the processing reaction can also be adjusted according to any given substrate. Preferably, the reaction is allowed to continue at a temperature between about 15° C. and about 45° C. More preferably, the temperature of the reaction is between about 20° C. and about 37° C., and most preferably the reaction occurs between about 25° C. and about 37° C. Once again, the skilled artisan will readily recognize that the reaction parameters of time, temperature and pH can be varied according to the needs of any desired precursor or processed polypeptide.

Any of a wide range of buffering agents can be employed, the only requirement being their ability to maintain a pH within the desired range. Examples of typical buffering agents are sodium phosphate, sodium acetate, sodium citrate, glycine, and the like. Preferred buffering agents are sodium acetate, sodium phosphate and glycine.

The precursor polypeptides for use in the present invention are generally prepared via recombinant DNA technology. In their preparation, a nucleotide sequence coding for the desired precursor polypeptide is prepared using routine techniques for such synthesis. These methods generally involve preparation of oligonucleotides coding both for fragments of the desired coding sequence and for their complementary sequence thereof. The oligonucleotides are designed to provide overlap of one fragment of the coding sequence with two fragments of the complementary sequence and vice versa. The oligonucleotides are paired and joined, ultimately producing the desired gene sequence.

The sequence is inserted into a cloning vector at a location which permits the product for which it codes to be expressed. A suitable cloning vector contains at least a portion of an expression control sequence.

The following Examples are provided as a means of illustrating the present invention. They are not to be construed as imposing a limitation thereon.

EXAMPLE 1

Fermentation of Dictyostelium discoideum

Lyophilized cultures of *Dictyostelium descoideum* Ax3 were obtained from the American Type Culture Collection in Rockville, Md. under the accession number ATCC 28368 and were plated at several densities on agar plates (1.2% Difco Bacto Agar) containing a buffered yeast extract-peptone medium composed of (g/l): Difco Yeast Extract (7.15), Difco Bacto Peptone (14.3), $Na_2HPO_4$ (0.51) and $KH2PO_4$ (0.49), to which Glucose (10g/l final) was added aseptically after separate sterilization and which was adjusted to a final pH of 6.5 (+/–0.1) with NaOH or $H_2SO_4$. This same media (without the agar) was used for liquid culture growth in volumes less than about one liter. The agar plates were incubated 3 to 5 days at 21° C. to 24° C. Spore sacks were harvested from the plate with care to prevent picking up the "food bacterium" lyophilized with the Ax3 culture, then inoculated in 3 ml of buffered yeast extract-peptone broth and incubated with gentle shaking at 21°–24° C. Thereafter, *D. discoideum* cells were amplified by serial transfer to progressively larger volumes of buffered yeast extract-peptone broth. Each serial transfer step was by a dilution between about 10- and 25-fold and occurred when cell densities exceeded about $2\times10^6$/ml. Broths were always incubated at 21°–24° C. with mild agitation.

Stirred fermentations were generally done in a similar medium with soy peptone (such as Phytone Peptone or Marcor Soy Peptone) at a concentration of 2 to 14.3 g/l substituted for the Bacto Peptone in the initial yeast extract-peptone medium. Harvests were usually from fermentors with a working volume from 10 to 5000 liters fitted with from 1 to 3 Rushton turbine impellors rotating at 40–150 RPM. Temperature was controlled at 22°+/–1° C., air flow controlled between 0.1 and 0.5 volumes air per volume of liquid broth and backpressure was maintained at 3–5 p.s.i. Some fermentations were done with pH controlled at 6.4 with sulfuric acid and some with dissolved oxygen controlled at 40–60% by varying agitation and air flow. Care was taken to minimize shear in handling and fermentation of the cells in that they are wall-less ameoba during growth.

In general, stirred cultures of *D. discoideum* Ax3 grew with doubling times between 12 and 36 hours. Dissolved oxygen decreased progressively (when not controlled) and then began to rise some time after cell density stopped increasing. Terminal cell densities ranged between $3\times10^6$/ml and $5\times10^7$/ml, with oxygen transfer apparently limiting in those fermentations with the lower maximum cell densities.

Samples were taken occasionally and analyzed for cell density and GF-pNAse activity (see Example 3, infra). A Petroff-Hauser counting chamber was used to estimate cell densities above approximately $5\times10^5$/ml. In general, GFpNA hydrolyzing activity increased throughout the fermentation. The maximum dDAP activity was seen 2 to 4 days after maximum cell density was reached. Whole broths were stored at 4° C. or frozen at –20° C. and later thawed and analyzed for activity. Fermentations were harvested by chilling to less than 10° C. and removing cells with a continuous-flow centrifuge.

EXAMPLE 2

Preparation of dDAP

A. Cell removal and concentration

Initial purification of dDAP from *Dictyostelium discoideum* fermentation broth involves cell removal and concentration steps. Cell removal was performed by continuous-flow centrifugation on a Western States centrifuge. The cell free media was concentrated about 20-fold by tangential flow ultrafiltration using a 50,000 molecular weight cut-off membrane. The retentate was drained from the ultrafiltration unit and the unit was washed with 50 mM tris buffer, pH 7, to recover additional dDAP. The retentate and wash samples were combined to form a final concentrate, which was stored frozen at –20° C. for several months before further processing occurred.

B. Clarification

The frozen final concentrate was thawed for about twelve hours at room temperature. Once thawed, the final concentrate was clarified prior to the first column chromatography step. Clarification was achieved by a combination of centrifugation followed by 5 micron membrane filtration. The clarified final concentrate was adjusted to pH 7.0 and held at 4° to 10° C. for less than 12 hours while awaiting the anion exchange chromatography step.

C. Anion Exchange Chromatography

The first chromatography step of the dDAP purification process was anion exchange chromatography using Pharmacia Q-Sepharose, trimethylaminomethyl substituted beaded agarose, Fast Flow resin (FFQ). The column was equilibrated with 50 mM tris buffer, pH 7. Clarified cell free concentrate was applied at 50 cm/hr linear flow rate at a ratio of 60 liters of unconcentrated fermentation media per liter of resin. This resulted in a protein charge of about 60 grams per liter resin (protein quantitation was based on the Pierce BCA Protein Assay against a standard of bovine serum albumin). About 250 units of dDAP activity were applied per liter of FFQ resin. The conductivity of the cell free concentrate was about 5 mMHOS per cm. After completing the sample charge, the FFQ resin was washed with three column volumes of equilibration buffer. The dDAP activity was eluted from the resin using a linear gradient of 0 to 1M NaCl, 50 mM tris, pH 7, applied over 10 column volumes at a flow rate of 50 cm/hr. Fraction size was 0.1 column volumes. The FFQ column was further eluted with three column volumes of 1.0M NaCl in 50 mM tris, pH 7. The effluent was monitored by conductivity and absorbance at 280 nm and fractions were assayed for dDAP activity by their ability to cleave the colorimetric substrate Gly-Phe para-nitroanilide (GFpNA) at pH 3.5. A mainstream pool was prepared by combining fractions containing about 90% of the total eluted dDAP activity. The dDAP activity eluted as a single peak about two column volumes in size. The mainstream pool was acidified to a pH of 3.5 using 10% v/v HCl. The FFQ acidified mainstream pool was held at 4° C. for less than two days.

D. Hydrophobic Interaction Chromatography

The FFQ acidified mainstream pool was next purified by hydrophobic interaction chromatography (HIC) on Pharmacia Phenyl Sepharose, phenyl sustituted beaded agarose, Fast Flow resin. The column was one-third the volume of the anion exchange column. About 650 units of activity were applied per liter of resin and the protein charge was 4 grams per liter of resin (1 absorbance unit at 280 nm was equated to 1 mg/ml protein). The FFQ mainstream was prepared for charge on to the HIC column by the addition of 140 grams per liter ammonium sulfate. The charge was adjusted to pH 3.5 and the final conductivity was about 90 mMHOS per cm. The HIC column was equilibrated in 50 mM citrate, pH 3.5, containing at least 140 grams per liter ammonium sulfate. The charge was applied at a linear flow rate of 40 cm/hr and the resin was washed with at least three column volumes of equilibration buffer. The dDAP activity was eluted from the resin using a linear gradient of 140 g per liter to 0 g per liter ammonium sulfate, in 50 mM citrate, pH 3.5, applied over 10 column volumes at 40 cm/hr. The column was further eluted with at least three column volumes of 50 mM citrate, pH 3.5. Fraction size was 0.1 column volumes. The effluent was monitored by conductivity and absorbance at 280 nm and fractions were assayed for dDAP activity by their ability to cleave GFpNA at pH 3.5. A mainstream pool was prepared by combining fractions containing about 90% of the total eluted dDAP activity. The dDAP activity eluted as a single peak about two column volumes in size. The mainstream pool was adjusted to a pH of 3.5 using 10% v/v HCl or 10% w/w NaOH. The HIC mainstream was held at 4° C. for less than one day before proceeding with processing.

E. Size Exclusion Chromatography

The HIC mainstream was further processed by size exclusion chromatography (SEC) on S-200 Sepharose, beaded agarose, HR. The column was twice the volume of the HIC column and had a bed height of 78 cm. The HIC mainstream was prepared for the SEC column by concentrating the HIC mainstream in an ultrafiltration unit using a membrane with a molecular weight cut-off of 10,000 daltons. The HIC mainstream was concentrated to 2.5% the SEC column volume and the retentate drained from the unit. The ultrafiltration unit was washed with a volume of 50 mM citrate buffer, pH 3.5, equal to 2.5% the SEC column volume. The retentate and the wash were combined to form a final concentrate and adjusted to pH 3.5 with 10% v/v HCl or 10% w/v NaOH. The conductivity of the final concentrate was about 30 mMHO per cm. The SEC column was equilibrated with 50 mM acetic acid, 20 mM sodium chloride, pH 3.5, which had a conductivity of about 2 mMHO per cm. The final concentrate was applied to the SEC column at 15 cm/hr linear flow and the dDAP activity was eluted by the application of one column volume of equilibration buffer. Fraction size was 0.02 column volumes. The effluent was monitored by conductivity and absorbance at 280 nm and fractions were assayed for dDAP activity by their ability to cleave GFpNA at pH 3.5. A mainstream pool was prepared by combining fractions containing about 90% of the total eluted dDAP activity. The dDAP activity eluted as a single peak of about 0.08 column volumes in size. The SEC mainstream pool may be held at 4° C. for several months.

Purification of dDAP using a combination of anion exchange, hydrophobic interaction, and size-exclusion chromatography resulted in material that migrated as a major band on SDS-PAGE. The band migrated to a position on the gel equivalent to the molecular weight standard bovine serum albumin (66 kilodaltons). The protein was stained using ISS Pro-blue stain. The migration pattern was unaffected by the presence or absence of 0.1M DTT (plus 100° C. for 5 minutes) during sample preparation. The subunit molecular weight of DAP-I (bovine source) is estimated by SDS-PAGE to be about 22,000 daltons.

EXAMPLE 3

Activity of dDAP

A. Conversion Reactions

1. Cleavage of GF-pNA dDAP activity is normally monitored by following the cleavage of the chromogenic substrate Gly-Phe para-nitroanilide (GF-pNA). Typically the assay is performed by diluting the enzyme 11 fold into 1.0 ml of 4 mM GFpNA adjusted to pH 3.5. The rate of cleavage of GF dipeptide was monitored at 37° C. by measuring the increase in absorbance at 405 nm. One unit of activity leads to a 0.90 OD change per minute under these conditions. Unit/ml estimates can be made assuming an extinction coefficient for free pNA of 9.9 mM-1 cm-1 at 405 nm.

The inhibition profile of dDAP toward the substrate GFpNA was compared to that of bovine DAP-I using iodoacetamide and potassium tetrathionate, sulfhydryl modifying agents known to inhibit the activity of DAP-I. Samples of dDAP or bovine spleen DAP-I were incubated for 15 minutes at room temperature in final concentrations of 0, 0.5, 5.0 or 50 mM of either inhibitor at pH 7 in 100 mM Tris buffer. The incubated solutions were then diluted 21-fold with 4 mM GFpNA, pH 3.5. The rate of cleavage was monitored by measuring the increase in absorbance at 405 nm at 37 degrees centigrade. Bovine DAP-I's rate of cleavage of GFpNA was decreased more than 90% by the exposure to 5 mM iodoacetamide and was 95% inhibited by 5 mM potassium tetrathionate. There was no evidence of significant inhibition of dDAP by any of the levels of iodoacetamide or potassium tetrathionate tested.

The pH optima for the GFpNA cleaving ability of dDAP was determined by adjusting a buffer consisting of 0.5 Tris, phosphate and citrate with 10% HCl or 10% NaOH to various pHs within the range of 3 to 8. dDAP enzyme was diluted 20-fold in a buffer containing 100 mM cysteamine and 10 mM NaCl. Bovine DAP-I was diluted 200-fold in the same buffer. A GFpNA substrate solution (4 mM) was prepared in 2% DMF. In a microtiter plate, 0.025 ml of the Tris/phosphate/Citrate buffer of various pH's was combined with 0.1 ml of diluted enzyme and with 0.1 ml of substrate solution. The rate of increase of absorbance at 410 nm was determined on a plate-reader over a 30 minute period. Results indicate that the pH optima of dDAP for the cleavage of GFpNA is between 3.5 and 4.0.

2. Cleavage of Gly-Arg-pNA

Four mM Gly-Arg-pNA (GR-pNA) was prepared in 50 mM acetic acid, 50 mM glycine buffer, pH 5. HCl or NaOH was used to achieve a variety of pHs, from 5.1 to 2.3. To 180 ul of the above pH buffered substrate was added 5 ul dDAP (49 milliunits/ml final). The rate of increase of absorbance at 410 nm was monitored (using a plate-reader) and the rate of increase was compared with the pH of the reaction solution. As with GF-pNA the GR-pNA substrate had a pH optimum around 3.5. The enzyme had little activity below pH 2.5 or above pH 5 using this substrate.

3. Cleavage of Arg-Arg-B-naphthlamide (RR-BNA)

About 0.25 mM RR-BNA or 0.25 mM Benzyloxycarbonyl-RR-BNA (Z-RR-BNA) was prepared in either 100 mM acetic acid, pH 3.5, or 100 mM citrate buffer, pH 5.0. To 2 ml of substrate was added dDAP or bovine DAP-I (about 15 milliunit/ml solution). Rates of cleavage (monitoring fluorescence increase at 410 nm with excitation at 340 nm) were monitored. Bovine DAP-I was unable to cleave either substrate. Surprisingly, dDAP was able to effectively cleave the RR-BNA substrate. dDAP was unable to cleave the blocked amino group Z-RR-BNA substrate, supporting the observation that dDAP is a DAP enzyme. The pH optimum for cleavage of RR-BNA was probed by monitoring the rate of RR-BNA cleavage using a buffer system consisting of 50 mM acetic acid and 50 mM citrate. Various pHs were achieved using HCl or NaOH and 1.5 ml volumes were made 2.0 with 0.5 ml of a 1 mM stock solution of RR-BNA (final concentration of about 0.25 mM). dDAP was added (to about 15 mU/ml) and the rates of cleavage were determined. The pH optimum for cleavage of RR-BNA was observed to be about 4.5, with significant activity seen over the entire range probed (pH 3.5 to pH 5.7). This surprising result suggests that dDAP shares some properties to that of DAP III.

The skilled artisan will recognize that the optimum pH for cleavage of a substrate not only depends upon the enzyme but the substrate itself, that is, the constitution of the removed dipeptide as well as the indicator group itself. For example, using dDAP, Gly-Arg-pNA has a pH optimum of about 3.5 while the pH optimum for cleavage of Gly-Arg-7-amido-4-methylcoumarin (GR-AMC) is about pH 5, suggesting that the reporting group can effect the cleavage properties.

B. Conversion of Synthetic Octapeptides and Decapeptides

The octapeptide Met-Asp-Phe-Pro-Ala-Met-Ser-Leu, SEQ ID NO:1, was dissolved to a concentration of 4 mM with 50 mM HOAc, pH 3.5. The solution was diluted 1:1 with dDAP (10mU/ml) and was incubated at room temperature for 6 hours. The reaction was quenched by diluting 20-fold in 7M urea containing 1% phosphoric acid. The quenched sample was analyzed by high performance reversed phase (HPLC) chromatography. Cleavage products were compared to standards of the octapeptide, the Met-Asp dipeptide, and the Phe-Pro-Ala-Met-Ser-Leu, SEQ ID NO:2, hexapeptide. dDAP readily removed the Met-Asp dipeptide from the unblocked aminoterminus of the octapeptide but was unable to readily cleave the emergent Phe-Pro dipeptide.

The synthesized decapeptide Met-Arg-Met-Tyr-Phe-Val-Asn-Gln-His-Leu, SEQ ID NO:3, was prepared as a 1.7 mM stock solution in 100 mM glycine, pH 3.5. To 0.5 milliliters of this solution was added 8 microliters of 6.4 mU/ml dDAP (prepared in 100 mM glycine, pH 3.5). Every hour 5 microliter of this solution was directly injected onto a reverse phase HPLC chromatographic system to monitor for cleavage products. Met-Arg and Met-Tyr dipeptides as well as Met-Tyr-Phe-Val-Asn-Gin-His-Leu, SEQ ID NO:4, and Phe-Val-Asn-Gln-His-Leu, SEQ ID NO:5, peptides were independantly injected for comparison. dDAP readily removed the Met-Arg dipeptide from the decapeptide, as well as the emergent Met-Tyr dipeptide. This indicates that dipeptides can be sequentially removed from the amino terminus by dDAP.

C. Conversion of Met-Asp-Human Growth Hormone

Met-Asp-Human Growth Hormone (Met-Asp-hGH) was produced as an insoluble protein in the cytoplasm of E. coli. The insoluble protein was solubilized, folded to produce proper disulfide-paired Met-Asp-hGH and purified by ion-exchange chromatography. This preparation was solvent exchanged and adjusted to pH 3.5. The Met-Asp-hGH was warmed to 37° C. and the absorbance at 280 nm was determined. dDAP was added at 6 milliunits per mg Met-Asp-hGH. The conversion reaction was allowed to proceed at 37° C. with stirring from about 4 to about 6 hours. The reaction process can be slowed without detriment by using less enzyme, lower temperature, or a lower Met-Asp-hGH concentration. Reaction rates can be increased by adding more enzyme, increasing the concentration of Met-Asp-hGH, or increasing the reaction temperature. Progress of the conversion reaction was monitored by reverse phase chromatorgraphy. The conversion reaction was terminated by the rapid addition of NaOH with stirring to pH 8 and by the addition of 30% v/v acetonitrile. The human growth hormone reaction product produced after dDAP treatment was subjected to an extensive battery of analytical procedures including peptide mapping, N-terminal sequencing, mass spectroscopy, amino acid analysis, and reverse phase chromatography (HPLC). All data indicated that authentic human growth hormone was produced by dDAP.

D. Conversion of Met-Arg-Human Proinsulin

Met-Arg-Human Proinsulin (Met-Arg-hPI) was produced as an insoluble protein in the cytoplasm of E. coli. The insoluble protein was solubilized in 7M urea. The protein was purified by ion exchange chromatography. The Met-Arg-hPI was sulfitolyzed, solvent exchanged and folded in order to form the native disulfide bond pairs and native tertiary structure. The material was further purified using reverse phase chromatography. The oxidized methionyl (Met O))-Arg-hPI was formed from Met-Arg-hPI using hydrogen peroxide and subsequently purified using reverse phase chromatography and lyophilized.

The Met-Arg-hPI was about 24 mg/ml (in approximately 20 mM glycine buffer, pH 3.5). About 2.4 mg of this material was incubated with 0.19 milliunits of dDAP at pH 3.5. The reaction was allowed to proceed at room temperature. Periodically, aliquots were removed and diluted with 10% phosphoric acid. This material was injected onto a neutral reverse phase HPLC system to monitor for the disappearance of Met-Arg-hPI or Met(O)-Arg-hPI and the subsequent production of hPI. In addition, aliquots were diluted into an appropriate diluent to allow for HPLC monitoring of appearance of either the Met-Arg or Met(O)-Arg dipeptides. Approximately 60% of the Met-Arg-hPI was converted to hPI in 8 hours. A similar result was unexpectedly seen for the Met(O)-Arg-hPI conversion experiment; that is, hPI was formed. The rate of cleavage of both substrates was similar. This result was surprising because bovine DAP-I appears to be unable to cleave Met(O)-X-derivatives of hPI, where X is Arg, Phe and Tyr. Reverse phase analysis also revealed that Met-Arg dipeptide was released from Met-Arg-hPI by comparison with reference Met-Arg dipeptide, and a peak appeared in the region of Met-Arg dipeptide for the experiment with the Met(O)-Arg-hPI substrate which could be the Met(O)-Arg dipeptide. The ability of dDAP to cleave the oxidized Met(O)-X substrate has distinct processing advantages over enzymes unable to perform this cleavage.

E. Conversion of Met-Arg-Human Proinsulin Analogs dDAP enzyme was also used to efficiently convert folded Met-Arg-Proinsulin Analog (B28 Lys, B29 Pro) as well as folded Met-Arg-Proinsulin Analog (B10 Asp, des B28–B30). These reactions were performed in substantial accordance with the teachings set forth in the explanations of the conversion of Met-Arg-hPI.

We claim:

1. A method for removing amino terminal dipeptides from a precursor polypeptide to produce a polypeptide product, which precursor polypeptide comprises an even number of amino acids extended from a peptide bond which is to be, after removal of said dipeptides, an amino terminus of said polypeptide product, said method comprising contacting said precursor polypeptide with an approximately 225 kilodalton dipeptidylaminopeptildase (dDAP) which is isolated from *Dictyostelium discoideum* and has a pH optimum of approximately 3.5, under conditions sufficient to allow the action of said dDAP to sequentially remove amino-terminal dipeptides from said precursor polypeptide to produce the polypeptide product.

2. A method for removing an amino-terminal dipeptide from a precursor polypeptide to produce a polypeptide product, which precursor polypeptide comprises a dipeptide extended from a peptide bond which is to be, after removal of said dipeptides, an amino terminus of said polypeptide product, said method comprising contacting said precursor polypeptide with an approximately 225 kilodalton dipeptidylaminopeptidase (dDAP) which is isolated from *Dictyostelium discoideum* and has a pH optimum of approximately 3.5, under conditions sufficient to allow the action of said dDAP to remove the amino-terminal dipeptide from said precursor polypeptide to produce the polypeptide product.

3. The method of claim 2 wherein the precursor polypeptide is selected from the group consisting of a precursor of human proinsulin, a precursor of human growth hormone, and a precursor of an analog of human proinsulin.

4. The method of claim 3 wherein said precursor polypeptide is a precursor of human proinsulin.

5. The method of claim 3 wherein said precursor polypeptide is a precursor of human growth hormone.

6. The method of claim 3 wherein said precursor polypeptide is a precursor of an analog of human proinsulin.

7. The method of claim 4 wherein the precursor of human proinsulin is Met-Tyr-Proinsulin.

8. The method of claim 4 wherein the precursor of human proinsulin is Met-Arg-Proinsulin.

9. The method of claim 5 wherein the precursor of human growth hormone is Met-Asp-Human Growth Hormone.

10. The method of claim 6 wherein the precursor of an analog of human proinsulin is [Lys$^{B28}$, Pro$^{B29}$]-Met-Arg-Proinsulin.

11. The method of claim 6 wherein the precursor of an analog of human proinsulin is [Lys$^{B28}$, Pro$^{B29}$]-Met-Tyr-Proinsulin.

12. The method of claim 6 wherein the precursor of an analog of human proinsulin is [Asp$^{B10}$, des B28–B30]-Met-Arg-Proinsulin.

13. The method of claim 6 wherein the precursor of an analog of human proinsulin is [Asp$^{B10}$, des B28–B30]-Met-Tyr-Proinsulin.

14. The method of claim 2 wherein said precursor polypeptide is contacted with said dDAP between about 1 minute and about 24 hours.

15. The method of claim 14 wherein said precursor polypeptide is contacted with said dDAP between about 1 and about 8 hours.

16. The method of claim 16 wherein said precursor polypeptide is contacted with said dDAP in a solution of between about pH 2.5 and about pH 5.5.

17. The method of claim 16 wherein said precursor polypeptide is contacted with said dDAP in a solution of between about pH 3.0 and about pH 4.5.

18. The method of claim 17 wherein said precursor polypeptide is contacted with said dDAP in a solution of between about pH 3.5.

19. The method of claim 2 wherein said precursor polypeptide is contacted with said dDAP at temperature of between about 15° C. and about 45° C.

20. The method of claim 19 wherein said precursor polypeptide is contacted with said dDAP at temperature of between about 20° C. and about 37° C.

21. The method of claim 20 wherein said precursor polypeptide is contacted with said dDAP at temperature of between about 25° C. and about 37° C.

22. The method of claim 2 wherein the N-terminal amino acid of said dipeptide is an oxidized methionine.

* * * * *